United States Patent
Shuber

(10) Patent No.: US 6,750,020 B2
(45) Date of Patent: *Jun. 15, 2004

(54) METHOD FOR ALTERATION DETECTION

(75) Inventor: Anthony P. Shuber, Mendon, MA (US)

(73) Assignee: Exact Sciences Corporation, Marlborough, MA (US)

( * ) Notice: Subject to any disclaimer, the term of this patent is extended or adjusted under 35 U.S.C. 154(b) by 140 days.

This patent is subject to a terminal disclaimer.

(21) Appl. No.: 09/988,491

(22) Filed: Nov. 20, 2001

(65) Prior Publication Data

US 2002/0132251 A1 Sep. 19, 2002

Related U.S. Application Data

(63) Continuation-in-part of application No. 09/809,713, filed on Mar. 15, 2001, now Pat. No. 6,428,964.

(51) Int. Cl.⁷ ............... C12Q 1/68; C12N 9/12; C07H 21/04; C07H 21/02
(52) U.S. Cl. ............ 435/6; 435/196; 536/23.1; 536/23.5; 536/23.7; 536/23.72
(58) Field of Search ............ 435/6, 196, 287.2, 435/288.7; 536/23.1, 24.3, 24.31, 24.32

(56) References Cited

U.S. PATENT DOCUMENTS

| | | | |
|---|---|---|---|
| 4,683,195 A | 7/1987 | Mullis et al. |
| 4,871,838 A | 10/1989 | Bos et al. |
| 5,098,823 A | 3/1992 | Bodmer et al. |
| 5,126,239 A | 6/1992 | Livak et al. |
| 5,137,806 A | 8/1992 | LeMaistre et al. |
| 5,202,231 A | 4/1993 | Drmanac et al. |
| 5,272,057 A | 12/1993 | Smulson et al. |
| 5,302,509 A | 4/1994 | Cheeseman |
| 5,330,892 A | 7/1994 | Vogelstein et al. |
| 5,348,855 A | 9/1994 | Dattagupta et al. |
| 5,382,510 A | 1/1995 | Levine et al. |
| 5,468,613 A | 11/1995 | Erlich et al. |
| 5,489,508 A | 2/1996 | West et al. |
| 5,512,441 A | 4/1996 | Ronal |
| 5,527,676 A | 6/1996 | Vogelstein et al. |
| 5,532,108 A | 7/1996 | Vogelstein |
| 5,545,527 A | 8/1996 | Stevens et al. |
| 5,552,283 A | 9/1996 | Diamandis et al. |
| 5,571,676 A | 11/1996 | Shuber |
| 5,578,458 A | 11/1996 | Caskey et al. |
| 5,582,989 A | 12/1996 | Caskey et al. |
| 5,589,330 A | 12/1996 | Shuber |
| 5,605,798 A | 2/1997 | Koster |
| 5,633,134 A | 5/1997 | Shuber |
| 5,645,986 A | 7/1997 | West et al. |
| 5,670,325 A | 9/1997 | Lapidus et al. |
| 5,698,400 A | 12/1997 | Cotton et al. |
| 5,707,806 A | 1/1998 | Shuber |

(List continued on next page.)

FOREIGN PATENT DOCUMENTS

| | | |
|---|---|---|
| AU | A-11325/95 | 4/1996 |
| EP | 0 332 435 B1 | 9/1989 |
| EP | 0 332 435 A2 | 9/1989 |

(List continued on next page.)

OTHER PUBLICATIONS

Aaltonen et al. (1994) "Replication Errors in Benign and Malignant Tumors from Hereditary Nonpolyposis Colorectal Cancer Patients" *Cancer Research* 54: 1645–1648.

(List continued on next page.)

Primary Examiner—Carla J. Myers
Assistant Examiner—Sally Sakelaris
(74) Attorney, Agent, or Firm—Testa, Hurwitz & Thibeault, LLP

(57) ABSTRACT

Methods are provided for detecting an alteration in a target nucleic acid. Methods of the invention are useful for detecting and identifying mutations that are indicative of disease or the predisposition for disease.

24 Claims, 3 Drawing Sheets

U.S. PATENT DOCUMENTS

| | | | | |
|---|---|---|---|---|
| 5,741,650 | A | 4/1998 | Lapidus et al. | |
| 5,759,777 | A | 6/1998 | Kearney et al. | |
| 5,811,239 | A | 9/1998 | Frayne | |
| 5,830,665 | A | 11/1998 | Shuber et al. | |
| 5,834,181 | A | 11/1998 | Shuber | |
| 5,846,710 | A | 12/1998 | Bajaj | |
| 5,849,483 | A | 12/1998 | Shuber | |
| 5,882,856 | A | 3/1999 | Shuber | |
| 5,888,778 | A | 3/1999 | Shuber | |
| 5,888,780 | A | 3/1999 | Dahlberg et al. | |
| 5,888,819 | A | 3/1999 | Goelet et al. | |
| 5,928,870 | A | 7/1999 | Lapidus et al. | |
| 5,952,178 | A | 9/1999 | Lapidus et al. | |
| 5,985,563 | A | * 11/1999 | Hyldig-Nielsen et al. | 435/6 |
| 6,013,431 | A | 1/2000 | Söderlund et al. | |
| 6,020,137 | A | 2/2000 | Lapidus et al. | |
| 6,025,127 | A | 2/2000 | Sidransky | |
| 6,048,689 | A | 4/2000 | Murphy et al. | |
| 6,051,378 | A | 4/2000 | Monforte et al. | |
| 6,074,823 | A | 6/2000 | Koster | |
| 6,100,029 | A | 8/2000 | Lapidus et al. | |
| 6,143,529 | A | 11/2000 | Lapidus et al. | |
| 6,146,828 | A | 11/2000 | Lapidus et al. | |
| 6,197,498 | B1 | 3/2001 | Koster | |
| 6,203,993 | B1 | 3/2001 | Shuber et al. | |
| 6,207,372 | B1 | 3/2001 | Shuber | |
| 6,214,558 | B1 | 4/2001 | Shuber et al. | |
| 6,221,601 | B1 | 4/2001 | Koster et al. | |
| 6,268,136 | B1 | 7/2001 | Shuber et al. | |
| 6,280,947 | B1 | 8/2001 | Shuber et al. | |
| 6,300,077 | B1 | 10/2001 | Shuber et al. | |
| 6,303,304 | B1 | 10/2001 | Shuber et al. | |
| 6,351,857 | B2 | 3/2002 | Slaon et al. | 4/315 |
| 6,406,857 | B1 | 6/2002 | Shuber et al. | 435/6 |
| 6,415,455 | B1 | 7/2002 | Slaon et al. | 4/315 |
| 6,428,964 | B1 | * 8/2002 | Shuber | 435/6 |
| 6,475,738 | B2 | 11/2002 | Shuber et al. | 435/6 |
| 6,482,595 | B2 | 11/2002 | Shuber et al. | 435/6 |
| 6,498,012 | B2 | 12/2002 | Laken | 435/6 |
| 6,503,718 | B2 | 1/2003 | Shuber et al. | 435/6 |
| 6,551,777 | B1 | 4/2003 | Shuber et al. | 435/6 |
| 6,586,177 | B1 | 7/2003 | Shuber | 435/6 |
| 2001/0018180 | A1 | 8/2001 | Shuber et al. | 435/6 |
| 2001/0039012 | A1 | 11/2001 | Lapidus | 435/6 |
| 2001/0042264 | A1 | 11/2001 | Sloan et al. | 4/315 |
| 2002/0001800 | A1 | 1/2002 | Lapidus | 435/6 |
| 2002/0004201 | A1 | 1/2002 | Lapidus et al. | 435/6 |
| 2002/0025525 | A1 | 2/2002 | Shuber | 435/6 |
| 2002/0040498 | A1 | 4/2002 | Sloan et al. | 4/315 |
| 2002/0045183 | A1 | 4/2002 | Shuber et al. | 435/6 |
| 2002/0048752 | A1 | 4/2002 | Lapidus et al. | 435/6 |
| 2002/0064787 | A1 | 5/2002 | Shuber et al. | 435/6 |
| 2002/0110810 | A1 | 8/2002 | Shuber | 435/6 |
| 2002/0119469 | A1 | 8/2002 | Shuber et al. | 435/6 |
| 2002/0119472 | A1 | 8/2002 | Lapidus et al. | 435/6 |
| 2002/0123052 | A1 | 9/2002 | Laken | 435/6 |
| 2002/0132251 | A1 | 9/2002 | Shuber | 435/6 |
| 2002/0164631 | A1 | 11/2002 | Shuber et al. | 435/6 |
| 2003/0044780 | A1 | 3/2003 | Lapidus et al. | 435/6 |
| 2003/0049659 | A1 | 3/2003 | Lapidus et al. | 435/6 |
| 2003/0087258 | A1 | 5/2003 | Shuber | 435/6 |

FOREIGN PATENT DOCUMENTS

| | | |
|---|---|---|
| EP | 0 390 323 A2 | 10/1990 |
| EP | 0 407 789 A1 | 1/1991 |
| EP | 0 407 789 B1 | 1/1991 |
| EP | 0 408 918 B1 | 1/1991 |
| EP | 0 408 918 A1 | 1/1991 |
| EP | 0 497 527 A1 | 8/1992 |
| EP | 0 608 004 A2 | 7/1994 |
| EP | 0 259 031 B1 | 11/1994 |
| EP | 0 664 339 A1 | 7/1995 |
| WO | WO 90/09455 | 8/1990 |
| WO | WO 91/13075 | 9/1991 |
| WO | WO 92/15712 | 9/1992 |
| WO | WO 93/20233 | 10/1993 |
| WO | WO 94/11383 | 5/1994 |
| WO | WO 95/07361 | 3/1995 |
| WO | WO 95/09928 | 4/1995 |
| WO | WO 95/12607 | 5/1995 |
| WO | WO 95/19448 | 7/1995 |
| WO | WO 96/12821 | 5/1996 |
| WO | WO 96/13611 | 5/1996 |
| WO | WO 97/23651 | 7/1997 |
| WO | WO 97/28450 | 8/1997 |
| WO | WO 98/38338 | 9/1998 |
| WO | WO 98/39478 | 9/1998 |
| WO | WO 98/58081 | 12/1998 |
| WO | WO 98/58084 | 12/1998 |
| WO | WO 99/20798 | 4/1999 |
| WO | WO 99/28507 | 6/1999 |
| WO | WO 99/53316 | 10/1999 |
| WO | WO 99/66077 | 12/1999 |
| WO | WO 00/09751 | 2/2000 |
| WO | WO 00/11215 | 3/2000 |
| WO | WO 00/31298 | 6/2000 |
| WO | WO 00/31303 | 6/2000 |
| WO | WO 00/31305 | 6/2000 |
| WO | WO 00/32820 | 6/2000 |
| WO | WO 00/50640 | 8/2000 |
| WO | WO 00/58514 | 10/2000 |
| WO | WO 00/61808 | 10/2000 |
| WO | WO 00/66005 | 11/2000 |
| WO | WO 00/70096 | 11/2000 |
| WO | WO 01/11083 | 2/2001 |
| WO | WO 01/18252 | 3/2001 |
| WO | WO 01/42502 | 6/2001 |
| WO | WO 01/42503 | 6/2001 |
| WO | WO 01/42781 | 6/2001 |
| WO | WO 01/64950 | 9/2001 |
| WO | WO 02/055740 | 7/2002 |
| WO | WO 02/059379 | 8/2002 |
| WO | WO 02/074995 | 9/2002 |
| WO | WO 02/092858 | 11/2002 |
| WO | WO 03/044217 | 5/2003 |
| WO | WO 03/071252 | 8/2003 |

OTHER PUBLICATIONS

Aaltonen et al. (1998) "Incidence of Hereditary Nonpolyposis Colorectal Cancer and the Feasibility of Molecular Screening for the Disease" *The New England Journal of Medicine* 338: 1481–1487.

Ausubel et al., (1995), *Short Protocols in Molecular Biology*, 3d ed., pp. 2–3–2–12, 3–30–3–33.

Bertario et al. (1999) "Risk of Colorectal Cancer Following Colonoscopic Polypectomy" *Tumori* 85: 157–162.

Blum, H.E., (1995) "Colorectal Cancer: Future Population Screening for Early Colorectal Cancer" *European Journal of Cancer*, vol. 31A, pp. 1369–1372.

Bos et al., (May 28, 1987) "Prevalence of ras Gene Mutations in Human Colorectal Cancers," *Nature*, vol. 327, pp. 293–297.

Caetano–Anollés (1993) Amplifying DNA with Arbitrary Oligonucleotide Primers, *PCR Methods and Applications, 3:85–94.*

Caldas, et al., (1994) Detection of K–ras Mutations in the Stool of Patients with Pancreatic Adenocarcinoma and Pancreatic Ductal Hyperplasia, *Cancer Research,* 54:3568–3573.

Capozzi et al. (1999) "Evaluation of the Replication Error Phenotype in Relation to Molecular and Clinicopathological Features in Hereditary and Early Onset Colorectal Cancer" *European Journal of Cancer* 35:289–295.

Cave et al., (1994) "Reliability of PCR Directly from Stool Samples: Usefulness of an Internal Standard," *BioTechniques*, vol. 16, No. 5, pp. 809–810.

Chapelle (1999) "Testing Tumors for Microsatellite Instability" *European Journal of Human Genetics* 7: 407–408.

Charlesworth et al., (Sep. 15, 1994) "The Evolutionary Dynamics of Repetitive DNA in Bukaryotes," *Nature* vol. 371, pp. 215–220.

Chen et al. (1997) "Microsatellite Instability in Sporadic-Colon–Cancer Patients With and Without Liver Metastases" *International Journal of Cancer* 74: 470–474.

Chen et al. (1997) "Fluorescence Energy Transfer Detection as a Homogeneous DNA Diagnostic Method", *Proc. Natl. Acad. Sci. USA*, 94: 10756–10761.

Coll et al., (Oct. 1989) "Evaluation of a Rapid Method of Extracting DNA from Stool Samples for Use in Hybridization Assays," *Journal of Clinical Microbiology*, vol. 27, No. 10, pp. 2245–2248.

Coughlin et al. (1999) "Public Health Perspectives on Testing for Colorectal Cancer Susceptibility Genes" *American Journal of Preventive Medicine* 16: 99–104.

Cunningham C. and M.G. Dunlop, (1996) "Molecular Genetic Basis of Colorectal Cancer Susceptibility," *British Journal of Surgery*, vol. 83, pp. 321–329.

Deng et al., (Dec. 20, 1996) "Loss of Heterozygosity in Normal Tissue Adjacent to Breast Carcinomas," *Science*, vol. 274, pp. 2057–2059.

Deuter et al., (1995) "A Method for Preparation of Fecal DNA Suitable for PCR," *Nucleic Acids Research*, vol. 23, No. 18, pp. 3800–3801.

Dib et al., (Mar. 14, 1996) "A Comprehensive Genetic Map of the Human Genome Based on 5,264 Microsatellites," *Nature* vol. 380, pp. 152–154.

Duffy M.J., (1995) "Can Molecular Markers Now be Used for Early Diagnosis of Malignancy?" *Clin. Chem,*. vol. 41, No.10, pp. 1410–1413.

Eguchi et al., (Apr. 15, 1996) "Mutations of the p53 Gene in the Stool of Patients with Resectable Colorectal Cancer," *Cancer Supplement*, vol. 77, No. 8, pp. 1707–1710.

Enari et al., (Jan. 1, 1998) "A Caspase–Activated DNase that Degrades DNA During Apoptosis, and its Inhibitor ICAD," *Nature*, vol. 391, pp. 43–50.

"Experimental Protocol", *Nature Biotechnology*, (Aug., 1999), vol. 17, p. 807.

Fearon, E.R., (1995) "16 Molecular Abnormalities in Colon and Rectal Cancer," *The Molecular Basis of Cancer*, pp. 340–357.

Fu, et al., (1995) A DNA Sequencing Strategy That Requires Only Five Bases of Known Terminal Sequence for Priming, *Proc. Natl. Acad. Sci. USA, 92:10162–10166.*

Grossman et al. (1988), "Colonscopic Screening of persons With Suspected Risk Factors for Colon Cancer" *Gastroenterology* 94: 395–400.

Gyllensten U.B., Allen M., (1995) "Sequencing of In Vitro Amplified DNA," *Recombinant DNA Methodology II*, (Wu, ed.), pp. 565–578.

Hasegawa et al., (1995) "Detection of K–ras Mutations in DNAs Isolated From Faces of Patients with Colorectal Tumors by Mutant–Allele–Specific Amplification (MASA)," *Oncogene*, vol. 10, pp. 1441–1445.

Hoang et al. (1997) "BAT–26, an Indicator of the Replication Error Phenotype in Colorectal Cancers and Cell Lines" *Cancer Research* 57: 300–303.

Honchel et al., (1995) "Genomic Instability in Neoplasia," *Seminars in Cell Biology*, vol. 6, pp. 45–52.

Hoss et al., (Sep. 17, 1992) "Excrement Analysis by PCR" *Scientific Correspondence* pp. 199.

Iino et al. (1999) "DNA Microsatellite Instability in Hyperplastic Polyps Serrated Adenomas, and Mixed Polyps: A Mild Mutator Pathway for Colorectal Cancer?" *Journal of Clinical Pathology* 52: 5–9.

Ikonen, et al., (1992) Quantitative Determination of Rare mRNA Species by PCR and Solid–phase Minisequencing, *PCR Methods and Applications 1:234–240.*

Iniesta et al. (1998) "Genetic Abnormalities and Microsatellite Instability in Colorectal Cancer" *Cancer Detection and Prevention* 22: 383–395.

Ishimaru et al. (1995) "Mmicrosatellite Instability in Primary and Metastatic Colorectal Cancers" *Int. J. Cancer (Pred. Oncol.)*, 64: 153–157.

Jarvinen et al. (1995) "Screening Reduces Colorectal Cancer Rate in Families With Hereditary Nonpolyposis Colorectal Cancer" *Gastroenterology* 108: 1405–1411.

Jernvall et al. (1999) "Microsatellite Instability: Impact on Cancer Progression in Proximal and Distal Colorectal Cancers" *European Journal of Cancer* 35, No. 2, pp. 197–201.

Jessup, J.M. and G.E. Gallick, (Sep./Oct. 1992) "The Biology of Colorectal Carcinoma," *Current Problems in Cancer* pp. 263–328.

Jonsson et al., (Jan. 1995) "From Mutation Mapping to Phenotype Cloning," *Proc. Natl. Acad. Sci. USA*, vol. 92 pp. 83–85.

Kieleczawa, et al., (1992) DNA Sequencing by Primer Walking with Strings of Contiguous Hexamers, *Science, 258:1787–1791.*

Kim et al. (1998) "Microsatellite Instability in Young Patients With Colorectal Cancer" *Pathology International* 48: 586–594.

Konishi et al. (1996) "Molecular Nature of Colon Tumors in Hereditary Nonpolyposis Colon Cancer, Familial Polyposis, and Sporadic Colon Cancer" *Gastroenterology* 111:307–317.

Kotler, et al., (1993) DNA Sequencing: Modular Primers Assembled from a Library of Hexamers or Pentamers, *Proc. Natl. Acad. Sci. USA, 90:4241–4245.*

Krook, et al., (1992) Rapid and simultaneous detection of multiple mutations by pooled and multiplex single nucleotide primer extension: application to the study of insulin-responsive glucose transporter and insulin reception in non-insulin–dependent diabetes, *Human Molecular Genetics, 1:391–395.*

Lamberti et al. (1999) "Microsatellite Instability—a Useful Diagnostic Tool to Select Patients at High Risk for Hereditary Non–Polyposis Colorectal Cancer: A Study in Different Groups of Patients With Colorectal Cancer"*Gut* 44: 839–843.

Lebacq, (1992) Polymerase chain reaction and other methods to detect hot–spot and multiple gene mutations, *Ann Biol Clin, 50:709–712.*

Lenguaer et al., (Dec. 17, 1998) "Genetic Instabilities in Human Cancers," *Nature*, vol. 396, pp. 643–649.

Leong et al., (1993) "Detection of MYCN Gene Amplification and Deletions of Chromosome 1p in Neuroblastoma by In Situ Hybridization Using Routine Histologic Sections," *Laboratory Investigation*, vol. 69, No. 1, pp. 43–50.

Lin et al. (1998) "Colorectal and Extracolonic Cancer Variations in MLH1/MSH2 Hereditary Nonpolyposis Colorectal Cancer Kindreds and the General Population" *Diseases of the Colon & Rectum* 41: 428–433.

Iitia et al., (1992) "Simultaneous Detection of Two Cystic Fibrosis Alleles Using Dual–Label Time–Resolved Fluorometry," *Molecular and Cellular Probes*, vol. 6, pp. 505–512.

Lleonart et al. (1998) "Microsatellite Instability and p53 Mutations in Sporadic Right and Left Colon Carcinoma" *Cancer*, 83: 889–895.

Loktionov A. and I. K. O'Neill, (1995) "Early Detection of Cancer–Associated Gene Alterations in DNA Isolated from Rat Feces During Intestinal Tumor Induction with 1,2–Dimethylhydrazine," *International Journal of Oncology*, vol. 6, pp. 437–445.

Loktionov et al., (Feb., 1998) "Quantitation of DNA from Exfoliated Colonocytes Isolated from Human Stool Surface as a Novel Noninvasive Screening Test for Colorectal Cancer," *Clinical Cancer Research*, vol. 4, pp. 337–341.

Mao L. et al., (Feb. 2, 1996) "Molecular Detection of Primary Bladder Cancer by Microsatellite Analysis," *Science*, vol. 271, pp. 659–662.

Myers, R.M., (Feb. 12, 1993) "The Pluses of Subtraction," *Science*, vol. 259, pp. 942–943.

Naber, S. P., (Dec. 1, 1994) "Molecular Pathology—Detection of Neoplasia," *The new England Journal of Medicine*, vol. 331, No. 22, pp. 1508–1510.

Nollau et al., (May 1996) "Isolation of DNA from Stool and Bodily Fluids for PCR Amplication," *BioTechniques*, vol. 20, No. 5, pp. 784–788.

Nollau et al., (1996) "Detection of K–ras Mutations in Stools of Patients with Colorectal Cancer by Mutant–Enriched PCR," *Int. J. Cancer*, vol. 66 pp. 332–336.

Orlow I., et al., (Dec. 18, 1995) "Deletion of the p16 and p15 Genes in Human Bladder Tumors *Journal of the National Cancer Institute*,," vol. 87, No. 20, pp. 1524–1529.

Park et al. (1999) "Gene–Environment Interaction in Hereditary Nonpolyposis Colorectal Cancer with Implications for Diagnosis and Genetic Testing" *International Journal of Cancer* 82: 516–519.

Peltomaki et al. (1997) "Mutations Predisposing to Hereditary Nonpolyposis Colorectal Cancer: Database and Results of a Collaborative Study" *Gastroenterology* 113: 1146–1158.

Pharmacia, (1998) *BioDirectory*, pp. 104–109.

Pharmacia, (1991/1992) *Molecular and Cell Biology Catalogue*, pp. 8.3–8.6.

Piao et al., (Sep. 1997) "Relationship between Loss of Heterozygosity of Tumor Suppressor Genes and Histologic Differentiation in Hepatocellular Carcinoma," *Cancer*, vol. 80, No. 5, pp. 865–872.

Ponz de Leon et al. (1998) "Frequency and Type of Colorectal Tumors in Asymptomatic High–Risk Individuals in Families with Hereditary Nonpolyposis Colorectal Cancer" *Cancer Epidemiology, Biomarkers & Prevention* 7: 639–641.

Ponz de Leon et al. (1999) "Hereditary Colorectal Cancer in the General Population: From Cancer Registration to Molecular Diagnosis" *Gut* 45: 32–38.

Pyatt et al. (1999) "Polymorphic Variation at the BAT–25 and BAT–26 Loci in Individuals of African Origin" *American Journal of Pathology* 155: 349–353.

Raff, M., (Nov. 12, 1998) "Cell Suicide for Beginners," *Nature*, vol. 396, pp. 119–122.

Rashid et al. (1999) "Genetic Epidemiology of Mutated K–ras Proto–Oncogene, Altered Suppressor Genes, and Microsatellite Instability in Colorectal Adenomas" *Gut* 44: 826–833.

Ravelingien et al., (1995) "Contribution of Molecular Oncology in the Detection of Colorectal Carcinomas," *Acta Gastro–Enterologica Belgica*, vol. 58, pp. 270–273.

Riegler et al. (1999) "Prevalence of HNPCC in a Series of Consecutive Patients on the First Endoscopic Diagnosis of Colorectal Cancer: A Multicenter Study" *Endoscopy* 31: 337–341.

Rhyu M. S., (Mar. 6, 1996) "Molecular Mechanisms Underlying Hereditary Nonpolyposis Colorectal Carcinoma," *Journal of the National Cancer Institute*, vol. 88, No. 5, pp. 240–251.

Ridanpaa et al., (1995) "Detection of Loss Heterozygosity in the p53 Tumor Suppressor Gene Using a PCR–based Assay," *Path. Res. Pract.*, vol. 191, pp. 399–402.

Rodriguez–Bigas et al. (1997) "A National Cancer Institute Workshop on Hereditary Nonpolyposis Colorectal Cancer Syndrome: Meeting Highlights and Bethesda Guidelines" *Journal of the National Cancer Institute* 89: 1758–1762.

Runnebaum, et al., (1994) Multiplex PCR Screening detects small p53 deletions and insertions in human ovarian cancer cell lines, *Human Genetics*, 93:620–624.

Salahshor et al. (1999) "Microsatellite Instability in Sporadic Colorectal Cancer is Not an Independent Prognostic Factor" *British Journal of Cancer* 81: 190–193.

Samowitz et al. (1995) "Microsatellite Instability in Human Colonic Cancer Is Not a Useful Clinical Indicator of Familial Colorectal Cancer" Gastroenterology 109: 1765–1771.

Samowitz et al. (1997) "Microsatellite Instability in Colorectal Adenomas" *Gastroenterology* 112: 1515–1519.

Samowitz et al. (1999) "BAT–26 and BAT–40 Instability in Colorectal Adenomas and Carcinomas and Germline Polymorphism" *American Journal of Pathology* 154: 1637–1641.

Sanger et al., (Dec. 1977) "DNA Sequencing with Chain–Terminating Inhibitors" *Proc. Natl. Acad. Sci. USA*, vol. 74, No. 12, pp. 5463–5467.

Segel I., (1968 and 1976), "Double Label Analysis," *Biochemical Calculations*, 2d ed., pp. 373–376.

Shumaker, et al., (1996) Mutation Detection by Solid Phase Primer Extension, *Human Mutation, 7:346–354*.

Sidransky, et al., (Apr. 3, 1992) "Identification of ras Oncogene Mutations in the Stool of Patients with Curable Colorectal Tumors," *Science*, vol. 256, pp. 102–105.

Smith–Ravin et al., (1995) "Detection of c–Ki–ras Mutations in Faecal Samples from Sporadic Colorectal Cancer Patients," *Gut*, vol. 36, pp. 81–86.

Syngal et al. (1998) "Benefits of Colonoscopic Surveillance and Prophylactic Colectomy in Patients With Hereditary Nonpolyposis Colorectal Mutations" *Ann Intern Med.* 129: 787–796.

Syngal et al. (1999) "Interpretation of Genetic Test Results for Hereditary Nonpolyposis Colorectal Cancer" *JAMA* 282: 247–253.

Syvänen, (1994) Detection of point mutations in human genes by the solid–phase minisequencing method, *Clinica Chimica Acta*, 226:225–236.

Takeda et al., (1993) "Detection of K–ras Mutation in Sputum by Mutant–Allele–Specific Amplification (MASA)," *Human Mutation*, vol. 2, pp. 112–117.

Thibodeau et al., (May 7, 1993) "Microsatellite Instability in Cancer of the Proximal Colon," *Science*, vol. 260, pp. 816–819.

Vasen et al. (1993) "Surveillance in Hereditary Nonpolyposis Colorectal Cancer: An International Cooperative Study of 165 Families" *Diseases of the Colon & Rectum* 36: 1–4.

Vasen et al. (1998) "A Cost–Effectiveness Analysis of Colorectal Screening of Hereditary Nonpolyposis Colorectal Carcinoma Gene Carriers" *Cancer*, 82: 1632–1637.

Vasen et al. (1999) "New Clinical Criteria for Hereditary Nonpolyposis Colorectal Cancer (HNPCC, Lynch Syndrome) Proposed by the International Collaborative Group on HNPCC" *Gastroenterology* 116: 1453–1456.

Villa et al., (May 1996) "Identification of Subjects at Risk for Colorectal Carcinoma Through a Test Based on K–ras Determination in the Stool," *Gastroenterology*, vol. 110, No. 5, pp. 1346–1353.

Vogelstein et al. (Aug., 1999) "Digital PCR," *Proc. Natl. Acad. Sci. USA*, vol. 96, pp. 9236–9241.

Wallace et al., (1979) "Hybridization of Synthetic Oligodeoxyribonucleotides to Φχ 174 DNA: the Effect of Single Base Pair Mismatch," *Nucleic Acids Research*, vol. 6, No. 11, pp. 3543–3557.

Walsh et al., (1992) "Preferential PCR Amplifications of Alleles: Mechanisms and Solutions," *PCR Methods and Applications*, pp. 241–250.

Wang et al., (May 15, 1998) "Large–Scale Identification, Mapping, and Genotyping of Single–Nucleotide Polymorphisms in the Human Genome," *Science*, vol. 280, pp. 1077–1082.

Watson et al., (Sep. 1994) "Isolation of Differentiality Expressed Sequence Tags from Human Breast Cancer," *Cancer Research*, 1;54 (17), pp. 4598–4602.

Wijnen et al. (1999) "Familial Endometrial Cancer in Female Carriers of MSH6 Germline Mutations" *Nature Genetics* 23: 142–144.

Young et al. (1992) "The Genetics, Epidemiology, and Early Detection of Gastrointestinal Cancers" *Current Opinion in Oncology*, vol. 4, pp. 728–735.

Zhou et al. (1997) "Allelic Profiles of Mononucleotide Repeat Microsatellites in Control Individuals and in Colorectal Tumors With and Without Replication Errors" *Oncogene* 15: 1713–1718.

Zhou et al. (1998) "Determination of the Replication Error Phenotype in Human Tumors Without the Requirement for Matching Normal DNA by Analysis of Mononucleotide Repeat Microsatellites" *Genes, Chromosomes & Cancer* 21: 101–107.

Bodmer, (1990) "Hereditary Colorectal Cancer" *Springer–Verlag*, pp. 36–42.

Parker et al. (1991) "Targeted Gene Walking Polymerase Chain Reaction" *Nucleic Acids Research*, vol. 19, No. 11, pp. 3055–3060.

Tisty et al. (1993) "Loss of Chromosomal Integrity in Neoplasia" *Cold Spring Harbor Symposia on Quantitative Biology*, pp. 645–654.

Tisty et al. (1994) "Genomic Integrity and the Genetics of Cancer" *Cold Spring Harbor Symposia on Quantitative Biology*, pp. 265–276.

Lisitsyn et al. (1994) "Detection of Genetic Loss in Tumors by Representational Difference Analysis" *Cold Spring Harbor Symposia on Quantitative Biology*, pp. 585–587.

Lisitsyn et al. (1995) "Comparative Genomic Analysis of Tumors: Detection of DNA Losses and Amplification" *Proc. Natl. Acad. Sci. USA*, vol. 92, pp. 151–155.

Friedrich et al. (1995) "Genomic Characterization of Type 2 Polioviruses Isolated from Vaccine–Associated Cases in Brazil" *Brazilian Journal of Medical and Biological Research*, vol. 28, pp. 733–742.

Schlegel et al. (1995) "Comparative Genomic in Situ Hybridization of Colon Carcinomas with Replication Error" *Cancer Research*, vol. 55, pp. 6002–6005.

Reid et al. (1996) "Comparative Genomic Hybridization Reveals a Specific Pattern of Chromosomal Gains and Losses During the Genesis of Colorectal Tumors" *Genes, Chromosomes & Cancer*, vol. 15, pp. 234–245.

* cited by examiner

METHOD FOR ALTERATION DETECTION

This is a continuation-in-part of prior application Ser. No. 09/809,713, filed on, Mar. 15, 2001, now U.S. Pat. No. 6,428,964 the entire disclosure of which is incorporated by reference herein.

FIELD OF THE INVENTION

The invention relates generally to methods for detecting an alteration in a target nucleic acid.

BACKGROUND OF THE INVENTION

Many diseases are associated with genomic instability. As such, instability markers have been proposed as diagnostics. For example, mutations are considered valuable markers for a variety of diseases, and have formed the basis for screening assays. Specific mutations might be a basis for molecular screening assays for the early stages of certain types of cancer. See, e.g., Sidransky, et al., *Science*, 256: 102–105 (1992). For example, mutations in the BRCA genes have been proposed as markers for breast cancer, and mutations in the p53 cell cycle regulator gene have been associated with the development of numerous types of cancers.

Early alteration detection allows early disease diagnosis, and thus also provides an avenue for intervention prior to the presentation of disease symptoms that often occurs after metastasis when a cure is less readily attainable. However, the detection of genetic mutations or other alterations is difficult, or impossible, in certain sample types. For example, the difficulty of isolating DNA from complex, heterogeneous samples makes identification of early-stage mutation difficult.

Therefore, there is a need in the art for efficient methods for determining the presence or absence of certain genetic mutations or other alterations in a target nucleic acid in a biological sample.

SUMMARY OF THE INVENTION

The invention provides methods for detecting an alteration in a target nucleic acid in a biological sample. According to the invention, a series of nucleic acid probes complementary to a contiguous region of wild type target DNA are exposed to a sample suspected to contain the target. Probes are designed to hybridize to the target in a contiguous manner to form a duplex comprising the target and the contiguous probes "tiled" along the target. An example of this duplex is shown in FIG. 1. If a mutation or other alteration exists in the target, contiguous tiling will be interrupted, producing regions of single-stranded target in which no duplex exists. This is shown in FIG. 2. Identification of one or more single-stranded regions in the target is indicative of a mutation or other alteration in the target that prevented probe hybridization in that region. For purposes of the present invention, a "tiled sequence" or "tiling" refers to the contiguous hybridization of probes to a target region, whether separated by single-stranded sequence or not.

Accordingly, in methods of the invention, a sample comprising a single-stranded target nucleic acid is exposed to a plurality of nucleic acid probes. In a preferred embodiment, the plurality of probes comprises probes that are complementary to different positions of the target such that hybridization of members of the plurality with a wild-type target results in a contiguous series of probes along at least a portion of the target sequence when the target is a wild-type target. Probes including RNA, DNA and/or Peptide Nucleic Acid (PNA) may be employed to hybridize to the target nucleic acid. It is not necessary to ligate the series of probes to form a continuous strand, although ligation may be performed at the discretion of the user.

When the target is a wild-type sequence, there will be no single-stranded portion in the region in which the probes are tiled. However, when a mutation or other alteration exists in the region of the target to which probes are directed, one or more of the probes will fail to hybridize, resulting in one or more single-stranded portion of the target region. Identification of this single-stranded region is, according to the invention, a positive assay for a mutation or other alteration in the target.

In a preferred embodiment, a single-stranded region indicative of a mutation in the target is detected by exposing the target, subsequent to probe hybridization, to an agent that selectively cleaves single-stranded nucleic acid. In a mutated target, methods of the invention produce more than one "tiled" duplex in the target region. Multiple double-stranded tiled duplexes result from cleavage of the target in the single-stranded region to which any probe failed to hybridize. Numerous cleavage enzymes are known which selectively cleave or degrade single-stranded nucleic acids (e.g., S1, MutY, MutS and Mungbean nuclease). Identification of a single contiguous duplex comprising the target and the contiguous tiled probes upon exposure to the selective cleavage or degradation agent is indicative of a wild-type (non-mutated) target region. Alternatively, the products of cleavage are measured to determine, for example, whether the molecular weight of the products is different than would be expected from a single contiguous duplex.

Also in a preferred embodiment, the assay described above is multiplexed in order to interrogate multiple targets simultaneously. As such, one can look for specific double-stranded cleavage products in order to identify the specific mutated target(s) or one can simply identify multiple cleavage products (resulting, as described above, from intervening single-stranded regions in the "tiled target") as evidence of a mutation at one of the interrogated targets. For example, multiple targets, each containing a so-called "hot spot" for mutation in cancer are interrogated, the production of a single-stranded target region after tiling being sufficient to result in a positive screen for cancer or pre-cancer.

Methods of the invention are also useful for detecting non-hybridized regions at the termini of a target. When a mutation occurs in a region of target to which a terminal tile would hybridize if the target is a wild-type target, the resulting degradation of the single-stranded terminus will not, as described above, produce multiple duplex products indicative of an intervening single-stranded region. Instead, the terminal single-stranded region will be cleaved or degraded, leaving the tiled portion of the target intact. In that case, the terminal mutation is identified in by the reduced expected molecular weight of the tiled target or by the activity of the degrading agent (e.g., an exonuclease).

Alternatively, a mutation or other alteration in the termini of a target may also be detected by evaluating both the sense strand and antisense strand of the target. According to methods of the invention, both the sense and antisense strands of the target are bound to a solid support by the same respective terminus; for example, both the sense and the antisense strands of the target are bound to a solid support by their respective 5' ends. Thereafter, the bound sense and antisense strands of the target are interrogated in solution. A terminal mutation on, for example, the unbound 3' end of the sense strand would go undetected, however, the mutation presents a duplex cleaved from the mutation site near the bound 5' end of the antisense strand. The mutation is detected when the solid support is removed and the duplex cleaved off of the antisense strand remains in solution. If only the sense strand were tested, then the mutation would go undetected, thus testing both the sense and the antisense strands avoids a false negative caused by a terminal mutation on one of the strands.

In another embodiment, the invention provides methods to avoid detecting a known polymorphism as a false positive for an alteration. One or more polymorphisms may be present in a region of the target nucleic acid. In that case, multiple probes are designed to hybridize to each of the polymorphic variants known to be present in the target region. The probe complimentary to the polymorphism variant that is present in the target will hybridize to the region of the polymorphism. Providing the range of variants complementary to the associated polymorphisms ensures that the polymorphism region is "tiled" and any positive signal detected indicates the presence of an alteration other than the associated polymorphism on the target nucleic acid.

Methods of the invention are also useful for detecting the presence, in a population, of one or more polymophisms on a target nucleic acid. A plurality of nucleic acid probes is complementary to a first variant of a target nucleic acid comprising a polymorphism such that hybridization of members of the plurality with the target comprising the polymorphism variant results in a contiguous series of probes along at least a portion of the target. When one or more other polymorphic variants are present in the region of the target to which the probes are directed, at least one of the probes will fail to hybridize at the site of the other polymorphic variant. After hybridization, a single-stranded portion of the target region is exposed at the site of, for example, a second polymorphic variant. Upon exposure to an agent that selectively degrades single-stranded nucleic acid, the polymorphic variant presents a duplex cleaved from, for example, the site of the second polymorphic variant. Accordingly, detection of a cleavage product is a positive assay for an alteration, in this case the one or more other polymorphic variants, in the target.

In another aspect, probes are designed to hybridize to the target such that gaps separate one or more of the hybridized probes from each other. According to this aspect of the invention, a sample comprising single-stranded target nucleic acid is exposed to a plurality of nucleic acid probes. The plurality comprises probes that are complementary to different positions on the target nucleic acid such that hybridization of members of the plurality with a wild-type target results in a series of probes, along at least a portion of the target sequence, some of which may be separated a gap. Preferably, the gaps are small enough to prevent the degradation agent from cutting at the gap. Accordingly, preferred gap separations are shorter than the probes, i.e., the probes have a higher number of base pairs then the gaps. In preferred embodiments, the gap separations range between about 1 base pair and about 3 base pairs in length. Alternatively, gaps can be between about 3 base pairs and 15 base pairs in length. According to the invention, a detection assay can be performed using a plurality of probes some of which are separated by gaps and some of which are not when hybridized to the target nucleic acid.

According to this aspect of the invention, the degradation agent that that is selected, or alternatively, the conditions employed with the agent, do not cleave the target nucleic acid at the single-stranded gaps. In some embodiments, milder degradation conditions that avoid degrading any single-stranded gap separations are employed. For example, the number of degradation agent units used are held at a temperature and for a time period appropriate to maintain the single-stranded gap separations between tiles. The degradation agent conditions simultaneously degrade larger single-stranded regions where one or more probes failed to hybridize due to an alteration in the target. Because the gap separations are not degraded, false positives created by gap separations between the probes are avoided. However, the conditions enable degradation of the target region where the probe failed to hybridize, avoiding a false negative. Thus, according to the invention, a positive assay for an alteration in a target nucleic acid may comprise gaps separating complementary probes hybridized to the target. Where gap separations are present between probes, the selected degradation agent, units of agent used, temperature and exposure time are selected to provide conditions that maintain single stranded gap separations and that simultaneously cleave a single stranded alteration region where a probe failed to hybridize. Steric hindrance can also be used to prevent cutting at the gaps.

In another embodiment of the invention, the probes may be designed such that they prevent adjacent hybridized probes from creating a stabilizing effect that results in a probe hybridizing at the site of an alteration in a region of the target nucleic acid. Accordingly, the probes themselves are altered to include between about 1 and about 10 Abasic sites on the 5' and/or the 3' end of one or more of the probes. Similarly, the probes may be altered to put between about 1 to about 10 DNA, RNA, or Peptide Nucleic Acids that do not match the target nucleic acid on the 5' and/or the 3' end, and that do not prevent the probe from hybridizing to its complementary target.

In a preferred embodiment, a target nucleic acid is bound to a solid-support at either its 3' or 5' terminus. Complementary probes are tiled along the length of the target as described above. A mutation is indicated when double-stranded hybridization products are detected in solution after the sample is treated with a degradation agent indicating that one or more tiling probes failed to hybridize to the target due to the mutation. More than one target nucleic acid from more than one source can be simultaneously screened by binding multiple target nucleic acids to solid supports. Also, double-stranded nucleic acid according to the invention can be melted by, for example, heating.

In the event that a mutation is detected on a target nucleic acid, the identity of the mutation is determined by any method known in the art, such as sequencing, mass spectroscopy, and others.

In a preferred embodiment, a biological sample is exposed to probes complementary to a target DNA under stringent hybridization conditions so that each probe will hybridize only to the wild-type target nucleic acid. Such conditions are well-known in the art. See, e.g., 2 Joseph Sambrook, Peter MacCallum, & David Russell, *Molecular Cloning: A Laboratory Manual* ch., 10 (3d ed. 2001), incorporated by reference herein. In one embodiment, the hybridization melting temperature of each probe is about the same. In another embodiment, the probes are between about 8 and about 30 nucleotides long. In one preferred embodiment, each probe is the same length i.e. composed of the same number of nucleotides.

Preferred biological samples are sputum, pancreatic fluid, bile, lymph, plasma, urine, cerebrospinal fluid, seminal fluid, saliva, breast nipple aspirate, pus, biopsy tissue, fetal cells, amniotic fluid, and stool.

In another embodiment, at least one of the tiling probes comprises a detectable label. Each probe may comprise a different detectable label, permitting the differential detection of the probes (i.e., for example, the different probes may comprise a nucleotide with a different radioactive isotope, a fluorescent tag, or a molecular weight modifying entity). Differential probe labeling allows the identification of the probe that did not anneal to its target in the case of a mutation.

In another embodiment, the target nucleic acid comprises a detectable label in the region at which a mutation is suspected. When the suspected mutation is present in the target, no probe will hybridize to the target and the region of the mutation comprising the detectable label will remain single stranded. Upon exposure to an agent that cleaves single-stranded nucleic acid, the single-stranded mutation region comprising the detectable label is degraded from the target. The absence of the label in the degradation products is indicative of the presence of a mutation in the region of the detectable label.

In another embodiment, a quencher is placed at one end and a reporter is placed at the other end of each of the probes such that the absence of hybridization of one probe results in the reporter of an adjacent probe failing to be quenched. Accordingly, an alteration is detected by the reporter signal. The reporter may be detected via a fluorescent plate reader or alternatively with a gel apparatus equipped with fluorescent detection.

In yet another embodiment, a catalyst is placed at one end and an inhibitor is placed at the other end of each of the probes such that the absence of hybridization of one probe results in the exposure an uninhibited catalyst. Accordingly, an alteration is detected by a signal (e.g., fluorescence) generated by addition of an enzyme catalyzed by the uninhibited catalyst.

In one embodiment, methods of the invention comprise detecting a mutation at a genetic locus that is associated with a disease, such as K-RAS, p53, APC, DCC, or BAT26. In a preferred embodiment, that mutation is associated with cancer, such as colon cancer, lung cancer, esophageal cancer, prostate cancer, breast cancer, pancreatic cancer, stomach cancer, liver cancer, or lymphoma.

A detailed description of certain embodiments of the invention is provided below. Further aspects and advantages of the invention are apparent upon consideration of the following drawings, description and claims.

DETAILED DESCRIPTION OF THE INVENTION

Figure 1:
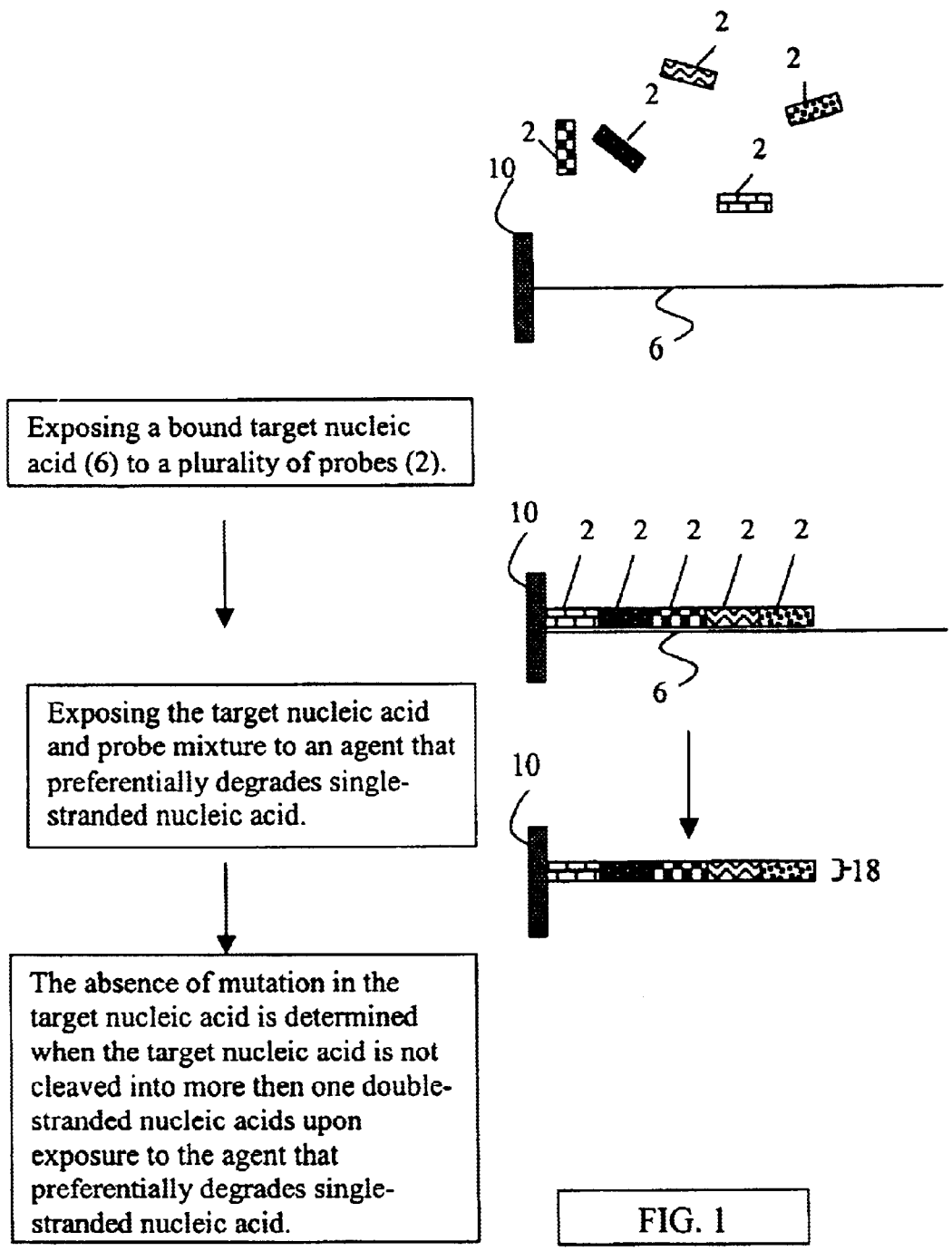
FIG. 1 shows a flow chart diagram that illustrates an embodiment of a method of the invention of detecting the absence of mutation in a target nucleic acid sample.

The present invention provides methods for detecting a genetic alteration in target nucleic acids indicative of genomic instability. For example, methods of the present invention are useful to detect and/or to identify mutations or other alterations associated with diseases, such as cancer and other pathological genetic conditions, disorders or syndromes. Such mutations include nucleotide insertions, deletions, rearrangements, transitions, translations, tranversions, polymorphisms, and substitutions. The present invention may be used to identify inherited mutations or other alterations. Generally, however, alterations include any change in the target nucleic acid, such as a mutation, loss of heterozygosity, or other indicia of genomic instability.

Methods of the invention rely upon the use of a plurality of probes, each probe comprises single-stranded nucleic acids and each probe is complementary to a different portion of a contiguous region of the target nucleic acid. According to the invention, each probe hybridizes to its complementary region on the target nucleic acid. When no mutation or other alteration is present in the target, the plurality of probes form a contiguous "tile" along the length of the target region. In the event that a portion of the target contains a mutation or other alteration, the target remains single-stranded in that region because the otherwise complementary probe will fail to hybridize in the presence of the mutation. Identification of the single-stranded region is indicative of a mutation or other alteration.

In a preferred embodiment, a single-stranded region indicative of a mutation or other alteration is detected by exposing the tiled target to an agent that preferentially degrades or cleaves single-stranded nucleic acid, and analyzing the degradation product(s). Exemplary degradation agents include chemical agents and enzymes, such as S1, MutY, MutS, and Mungbean nuclease. The presence of a singular intact double-stranded nucleic acid product is indicative of the absence of a mutation in any of the regions of the target nucleic acid (i.e., no cleavage of the target due to the absence of a single-stranded portion). The presence of two or more double-stranded products is indicative of the presence of a mutation or other alteration in one or more of the regions of the target nucleic acid (evidencing cleavage of the target at the single-stranded region(s) containing the mutation).

Biological samples that are useful in the present invention include any sample from a patient in which a target nucleic acid is present. Such samples are prepared from any tissue, cell, or body fluid. Examples of biological cell sources include blood cells, colon cells, buccal cells, cervicovaginal cells, epithelial cells from urine, fetal cells or cells present in tissue obtained by biopsy. Exemplary tissues or body fluids include sputum, pancreatic fluid, bile, lymph, plasma, urine, cerebrospinal fluid, seminal fluid, saliva, breast nipple aspirate, pus, amniotic fluid and stool. Useful biological samples also include isolated nucleic acid from a patient. Nucleic acid can be isolated from any tissue, cell, or body fluid using any of numerous methods that are standard in the art. The particular nucleic acid isolation method will depend on the source of the patient sample.

The biological sample comprising a target nucleic acid may be analyzed by methods of the present invention without further preparation or purification. In a preferred embodiment, one or more specific regions present in the target nucleic acid may be amplified by, for example, PCR. Concentrating the target nucleic acid by amplification improves accuracy by reducing background noise in the sample.

In one embodiment, the target nucleic acid is bound to a solid phase or semi-solid phase matrix. Support binding allows the simultaneous processing and screening of a plurality of nucleic acid samples from different sources, and allows degradation products to be compared in the liquid phase. Exemplary matrices suitable for use in the present invention include nitrocellulose or nylon filters, glass beads, magnetic beads coated with agents for affinity capture, treated or untreated microtiter plates, polymer gels, agarose and the like. It will be understood by a skilled practitioner that the method by which the target nucleic acid is bound to the matrix will depend on the particular matrix used. For example, binding to nitrocellulose can be achieved by simple absorption of nucleic acid to the filter followed by baking the filter at 75°–80° C. under vacuum for 25 minutes to 2 hours. Alternatively, charged nylon membranes that do not require any further treatment of the bound nucleic acid can be used. Beads and microtiter plates that are coated with avidin can be used to bind target nucleic acid to which biotin is attached (by, for example, the use of biotin-conjugated PCR primers). In addition, antibodies can be used to attach target nucleic acid to any of the above solid supports by coating the surfaces with an antibody and incorporating an antibody-specific hapten into the target nucleic acid. Excess binding agents are removed from the bound target nucleic acid by washing with appropriate buffers.

In practicing the present invention, the target nucleic acid, preferably bound to a solid phase or semi-solid phase matrix, is incubated with a plurality of nucleic acid probes. The length of individual probes may be 8–100 nucleotides. In a preferred embodiment, individual probes are 8–30 nucleotides in length. Probes comprising RNA, DNA, and/or Peptide Nucleic Acid (PNA) may be employed to hybridize to the target nucleic acid. The probes may be synthesized chemically by methods that are standard in the art, e.g., using commercially-available automated synthesizers. One or more of the probes may be labeled. For example, fluorochromes (such as FITC or rhodamine), enzymes (such as alkaline phosphatase), biotin, or other well-known labeling compounds may be attached directly or indirectly. Alternatively, the probes may be radioactively labeled (e.g., end-labeled with $^{32}P$ using polynucleotide kinase) or conjugated to other commonly used labels or reporter molecules. Further, these oligonucleotides can be marked with a molecular weight modifying entity (MWME) that uniquely identifies each of the probes.

As described in Shuber et al., *Human Molecular Genetics*, 2:153–158, (1993), incorporated by reference herein, the hybridization reaction can be performed under conditions in which probes having different nucleic acid sequences hybridize to their complementary DNA with equivalent strength. This is achieved by: 1) employing probes of equivalent length; and 2) including in the hybridization mixture appropriate concentrations of one or more agents that eliminate the disparity in melting temperatures ($T_m$) among probes of identical length but different guanosine+cytosine (G+C) content. Thus, under these conditions, the hybridization melting temperatures ($T_m$) of each member of the plurality of single-stranded nucleic acids is approximately equivalent. Agents that may be used for this purpose include quaternary ammonium compounds such as tetramethylammonium chloride (TMAC).

TMAC reduces hydrogen-bonding energy between G-C pairs. At the same time, TMAC increases the thermal stability of hydrogen bonds between A-T pairs. Those opposing influences reduce the difference in normal bond strength between the triple-hydrogen bonded G-C based pair and the double-hydrogen bonded A-T pair. TMAC also increases the slope of the melting curve for each probe. Together, those effects allow the stringency of hybridization to be increased to the point that single-base differences can be resolved, and non-specific hybridization minimized. See, e.g., Wood et al., *Proc. Natl. Acad. Sci., U.S.A.* 82:1585, (1985), incorporated by reference herein. Any agent that exhibits those properties can be employed in practicing the present invention. Such agents are easily identified by determining melting curves for different test probes in the presence and absence of increasing concentrations of the agent. This can be achieved by attaching a target nucleic acid to a solid matrix such as a nylon filter, individually hybridizing radiolabeled probes of identical lengths but different G+C content to the filter, washing the filter at increasing temperatures, and measuring the relative amount of radiolabeled probe bound to the filter at each temperature. Any agent that, when present in the hybridization and washing steps described above, results in approximately superimposable and steep melting curves for the different oligonucleotides may be used.

In practicing the present invention, the target nucleic acid and probes are incubated for sufficient time and under appropriate conditions to maximize specific hybridization and minimize non-specific hybridization. The conditions to be considered include the concentration of each probe, the temperature of hybridization, the salt concentration, and the presence or absence of unrelated nucleic acid.

The concentration of each probe generally ranges from about 0.025 to about 0.2 pmol per ml of hybridization solution. In one embodiment, each of the probes comprises an equal number of nucleotides. The probe sequences are designed to hybridize to consecutive, adjacent regions of the target nucleic acid. The optimal concentration for each probe can be determined by test hybridizations in which the signal-to-noise ratio (i.e., specific versus non-specific binding) of each probe is measured at increasing concentrations of labeled probes.

The temperature for hybridization can be optimized for the length of the probes being used. This can be determined empirically, using the melting curve determination procedure described above. It will be understood by skilled practitioners that hybridization condition determination of optimal time, temperature, probe concentration, salt type, and salt concentration should be done in concert.

According to the methods of the present invention, tiling probes hybridize only to their complementary region on the target nucleic acid. Thus, the target nucleic acid will remain single-stranded at any locus at which a mutation is present because no probe will hybridize at that locus. An exemplary alteration includes a single nucleotide polymorphism. Following hybridization, unbound probes are, if necessary, removed by washing under conditions that preserve perfectly matched target nucleic acid:probe hybridization products. Washing conditions such as temperature, time of washing, salt types and salt concentrations are determined empirically as described above.

Methods of the invention also avoid known polymorphisms being detected as a false positive for an alteration. Where one or more polymorphisms are associated with a region of the target nucleic acid, multiple probes, each designed to hybridize to one of the polymorphic variants are provided. A probe complimentary to a polymorphic variant on the target will hybridize to the region of the polymorphism. Thus, according to the method, probes are designed to block the polymorphic variants such that where the target is otherwise unaltered, the probes hybridize contiguously to a region of the target nucleic acid. Thus, providing probes complementary to each polymorphic variant ensures that the polymorphic region is "tiled" and any single-stranded regions detected according to the method indicate the presence on the target nucleic acid of an alteration other then an associated polymorphic variant.

In another aspect, probes are designed to hybridize to the target such that gaps separate one or more of the hybridized probes. According to this aspect of the invention, a sample comprising single-stranded target nucleic acid is exposed to a plurality of nucleic acid probes. The plurality comprise probes that are complementary to different positions of the target nucleic acid such that hybridization of members of the plurality with a wild-type target results in a series of probes, along at least a portion of the target sequence, that are separated by a gap of single-stranded nucleic acid. The gaps are sized such that the probes are longer then the gap separations, i.e., the probes have a higher number of base pairs then the gaps. In some embodiments, the gaps range between about 1 base pair and about 3 base pairs in length. Alternatively, gaps can range between about 3 base pairs and about 15 base pairs in length.

According to this aspect of the invention, the agent that that is selected, or alternatively, the conditions employed with the agent, do not cleave the target nucleic acid at the single-stranded gap separations. In some embodiments, a milder degradation agent is employed under conditions selected to avoid degrading single-stranded gap separations, such as, for example, the agent Mungbean nuclease is exposed at a temperature of about 37° C. for a period of about 10 minutes. Where gap separations are present between probes, the selected degradation agent, units of agent used, temperature and exposure time are selected to provide conditions that maintain (i.e., do not cut) single-stranded gap separations in the nucleic acid. However, the selected conditions degrade the single-stranded region of the nucleic acid where one or more probes failed to hybridize due to an alteration in the target. Because the gap separations do not degrade, false positives created by gap separations between the probes are avoided. However, the conditions enable degradation of the region of single-stranded nucleic acid on the target where the probe failed to hybridize, avoiding a false negative. Thus, according to the invention, a positive assay for an alteration in a target nucleic acid may comprise single-stranded gaps on the target separating complementary probes hybridized to the target.

In one embodiment, the target nucleic acid is present at a higher concentration than each individual probe, at least one of which is labeled with, for example, a fluorescent label that can be detected by excitation at the specific absorption wavelength from a light source in a spectrophotometer (fluorescent reporter). The hybridization products are removed from the solution, and the solution is evaluated for fluorescence. If no mutation is present in the target nucleic acid, no labeled probe should remain in the solution as all of the labeled probes will be bound to the target nucleic acid. Thus, the absence of mutation in the target nucleic acid is indicated if the solution does not fluoresce at an appreciable level. Alternatively, if the target nucleic acid is solid-support bound, the fluorescence of hybridized nucleic acid in solution after exposure to a degradation agent is indicative of the presence of a mutation in the target nucleic acid.

In another embodiment, the probe is radioactively labeled or chemiluminescent probes are employed and the presence of a mutation in the target nucleic acid is determined by exposure to X-ray film. Alternatively, or in addition, probes may carry a molecular weight modifying entity (MWME) that is unique for each probe. Such an entity allows direct identification of the separated probe by determination of the relative molecular weight by any number of methods.

While immobilization of the target nucleic acid is generally preferred, in some embodiments it may be desirable to hybridize the tiling probes to the target nucleic acid in solution. After exposing the hybridization product in solution to a degradation agent that preferentially degrades single-stranded nucleic acid, the degradation product(s) is analyzed by methods of the art that include SDS polyacrylamide gel electrophoresis, mass spectrophotometer, chromatography, hybridization capture and others. See, Ausubel et al., *Short Protocols in Molecular Biology, 3rd ed.* (John Wiley & Sons, Inc., 1995); Wu *Recombinant DNA Methodology II*, (Academic Press, 1995).

After detection of a mutation, the region, or genetic locus in the target nucleic acid where the mutation is present may be determined by identification of specific probes that failed to hybridize to the target nucleic acid. For example, in one embodiment, the hybridization product is cleaved into two separate double-stranded nucleic acids upon treatment with a degradation agent that preferentially degrades single-stranded nucleic acid. The two nucleic acids are separated and sequenced according to methods known in the art. The relative location and identity of the probes that successfully hybridize to the target nucleic acid can then be determined. Through the process of elimination, the one or more probes that failed to hybridize can be identified, as well as their relative position on the target nucleic acid. The genetic locus having a mutation will have a corresponding wild-type that is complementary to the probe that failed to hybridize.

FIG. 1 shows a flowchart diagram illustrating an embodiment of the present invention. As shown in FIG. 1, the absence of a mutation in a target nucleic acid is determined when the target nucleic acid is not cleaved into two or more double stranded fragments. In general overview the method comprises the steps of: exposing a bound target nucleic acid to a plurality of probes; exposing the target nucleic acid and probe mixture to an agent that preferentially degrades single-stranded nucleic acids; and determining that there is an absence of a mutation in the target nucleic acid if a singular intact double-stranded nucleic acid product is present in the sample after exposure to the degradation agent.

More specifically, the target nucleic acid (6) is bound to a solid phase or semi-solid phase matrix (10). The target nucleic acid is exposed to a plurality of probes (2) that are labeled with, for example, a fluorescent molecule. The target nucleic acid (6) and the plurality of probes (2) are incubated under optimal time, temperature, probe concentration, salt type, and salt concentration conditions. Stringent hybridization conditions that maximize specific hybridization by improving bonding energy symmetry and providing similar melting temperatures for each probe are employed. Those hybridization conditions enable only complementary probes to hybridize to the target nucleic acid. The target nucleic acid (6) and probe (2) mixture is then exposed to a degradation agent that preferentially degrades single-strand nucleic acid. The agent may be, for example, S1 nuclease.

The hybridization product comprising the target nucleic acid and probes (18) is then removed by its bound end from solution. The use of bound target nucleic acid enables a number of samples to be screened simultaneously by removing the bound portion from solution then analyzing the solution phase for degradation product indicative of a mutation.

Figure 2:
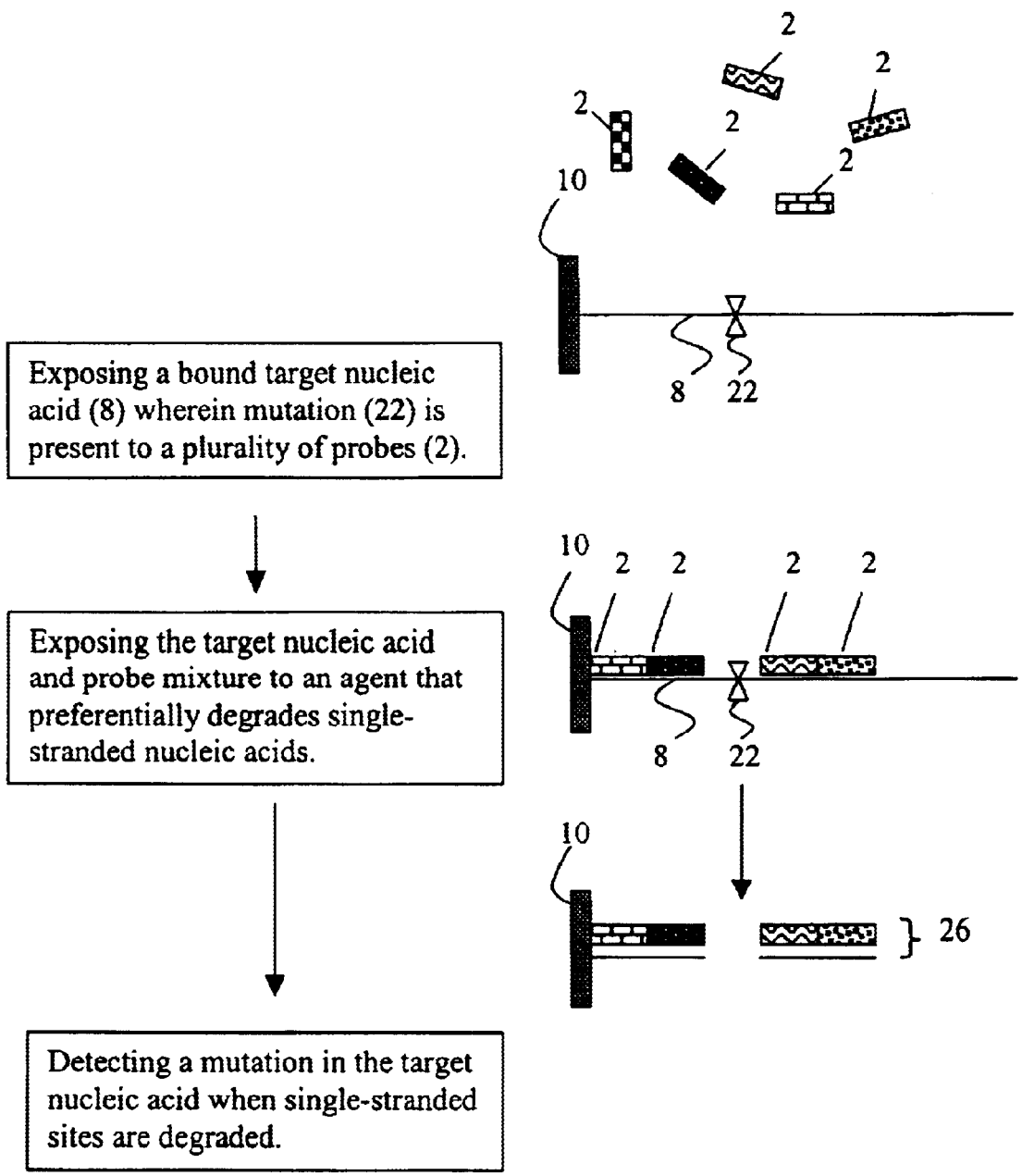
FIG. 2 shows a flow chart diagram that illustrates an embodiment of a method of the invention of detecting the presence of mutation in a target nucleic acid sample.

FIG. 2 shows a flowchart diagram illustrating another embodiment of the present invention. In general overview, the method comprises the steps of: exposing a bound target nucleic acid having a region at which a mutation is present to a plurality of probes; exposing the hybridized target nucleic acid and probe mixture to a degradation agent that preferentially degrades single-stranded nucleic acids; and detecting the presence of mutation in the target nucleic acid when a single-stranded region is degraded.

More specifically, the target nucleic acid (8) having a region with a mutation (22) is bound to a solid phase or semi-solid phase matrix (10). The target nucleic acid (8) is exposed to a plurality of probes (2) that are labeled by, for example, fluorescence. The target nucleic acid (8) and the plurality of probes (2) are incubated under optimal time, temperature, oligonucleotide concentration, salt type, and salt concentration conditions. Stringent hybridization conditions that maximize specific hybridization by improving bonding energy symmetry and providing similar melting temperature for each probe are employed. The hybridization conditions enable only complementary probes to hybridize to the target nucleic acid. Because no probe will be complementary to the region having a mutation (22), hybridization will not occur at that region, and the region will remain single-stranded.

After exposure to a degradation agent that preferentially degrades single-strand nucleic acid, the hybridization product is removed from solution by its bound end. The use of bound target nucleic acid enables a number of samples to be screened simultaneously by removing the bound portion from solution and then analyzing the solution phase for segments of hybridized (i.e., double-stranded) degradation product (26) indicative of the presence of a mutation in the target nucleic acid. The presence of one or more segments of hybridized degradation product (26) in solution is indicative that the target nucleic acid comprises a region having mutation (22) that was degraded by the degradation agent. The mutation is detected by exposing the solution to a light source in a spectrophotometer at the specific absorption wavelength, which reveals the appreciable quantities of fluorescing degradation product (26) indicative of a mutation (22).

The following example illustrates methods of the invention useful to detect a mutation in the mutation cluster region of the APC in samples prepared from stool.

EXAMPLE 1

Mutation Detection in the APC Mutation Cluster Region

Methods of the invention are used to detect the C→T point mutation at codon 1450 in the APC mutation cluster region, at http://perso.curie.fr/Thierry.Soussi/APC.html (last visited Feb. 20, 2001). Any biological sample that comprises APC may be used, including, for example, a stool sample. For the analysis of stool samples, preferred methods of the invention comprise obtaining at least a cross-section or circumferential portion of a voided stool as taught in U.S. Pat. Nos. 5,741,650, and 5,952,178, both of which are incorporated by reference herein. While a cross-sectional or circumferential portion of stool is desirable, methods provided herein are conducted on random samples obtained from voided stool, which include smears or scrapings. Once obtained, the stool specimen is homogenized. A preferable buffer for homogenization is one that contains at least 16 mM ethylenediaminetetraacetic acid (EDTA), as taught in co-pending, co-owned U.S. patent application Ser. No. 09/491,093, incorporated by reference herein. It has been discovered that the use of at least 16 mM EDTA, and preferably 100 mM EDTA or greater improves the yield of nucleic acid from stool. Thus, a preferred buffer for stool homogenization comprises phosphate buffered saline, 20–100 mM NaCl or KCl, at least 16 mM EDTA, and optionally a detergent (such as SDS) and a proteinase (e.g., proteinase K).

After homogenization, nucleic acid is preferably isolated from the stool sample. Isolation or extraction of nucleic acid is not required in all methods of the invention, as methods of the invention can be adequately performed in homogenized stool without isolation of nucleic acids. In a preferred embodiment, however, homogenized stool is spun to create a supernatant containing nucleic acids, proteins, lipids, and other cellular debris. The supernatant is treated with a detergent and proteinase to degrade protein, and the nucleic acid is phenol-chloroform extracted. The extracted nucleic acids are then precipitated with alcohol. Other techniques can be used to isolate nucleic acid from the sample. Such techniques include hybrid capture, and amplification directly from the homogenized stool. Nucleic acids can be purified and/or isolated to the extent required by the screening assay to be employed.

The nucleic acid is then mixed with steptavidin coated Dynal beads, which provides a solid phase matrix. The nucleic acid and bead mixture is vortexed and incubated which binds the beads to the nucleic acid. The nucleic acid can be amplified by PCR, which requires the nucleic acid template to be mixed with binding and wash buffers. The nucleic acid mixture is vortexed. The supernatant is removed, and buffer is added. These steps are then repeated a number of times.

Nucleic acid probes designed to complement consecutive regions of the known APC mutation cluster region are employed. The probes are uniform in length and are fluorescently labeled. The probe and the target nucleic acid comprising a point mutation in codon 1450 are incubated under conditions that maximize hybridization selectivity. Probe melting temperature disparities are eliminated, improving selectivity, when a suitable combination of hybridization temperature, time, probe concentration, salt type and salt concentration conditions are employed. TMAC is the agent selected to improve hybridization selectivity.

The probes are designed to detect mutations at codon 1450 in the APC mutation cluster region. When hybridizing under these selective hybridization conditions, the presence of a single mutation in the mutation cluster region will prevent the complementary probe from hybridizing, such that a portion of the region remains single stranded.

Consecutive complementary probes are designed to hybridize to the wild type APC mutation cluster region where the 5' end of that region is (5'-CTCCACCACCTCCTCAA ACAGCTCAAACCAAGCG AGAAGTACCTAAAAATA -3', SEQ ID NO:1).

In the experiment, each probe comprises 17 nucleotides, and the 5' end of the complementary probe designed for the region of codon 1450 is (5'-CGCTTGGTTTGAGCTGT-3', SEQ ID NO: 2). The complimentary probe upstream of the codon 1450 point mutation region is (5'-TTGAGGAGGTGGTGGAG-3', SEQ ID NO: 3). The complimentary probe downstream of the 1450 point mutation region is (5'-TATTTTTAGGTACTTCT-3', SEQ ID NO: 4). The probes and the target nucleic acid sample comprising the point mutation at codon 1450 in the mutation cluster region are incubated under conditions that maximize hybridization selectivity. The probe complimentary to the wild type region, SEQ ID No. 2, will not hybridize to the sequence comprising the point mutation at codon 1450 (C→T at the codon 1450 point mutation), (5'-

ACAGCTCAAACCAAGTG-3', SEQ ID NO:5). The point mutation at codon 1450 prevents hybridization and the portion of the APC region containing the mutation will remain single stranded.

After hybridization, unhybridized probes are removed by washing the nucleic acid mixture under time, temperature, salt type and salt concentration conditions that preserve the nucleic acid:probe hybrids. Exposure to the enzyme S1 cleaves the target nucleic acid at the single-stranded region comprising the point mutation at codon 1450, where the complimentary probe failed to hybridize.

The degradation products are separated by gel electrophoresis and analyzed using a spectrophotometer. The presence of mutation is detected by the presence of one or more degradation products, each comprising double-stranded nucleic acids which fluoresce upon excitation at the appropriate spectrophotometer wavelength.

EXAMPLE 2

Probes Blocking Polymorphic Variants at Codon 1493

Generally, a single nucleotide polymorphism is associated with each region having 1,000 nucleotide base pairs. According to methods of the invention, associated polymorphic variants are factored into probe design such that associated polymorphisms are "blocked" and other alterations may be detected.

Figure 3:
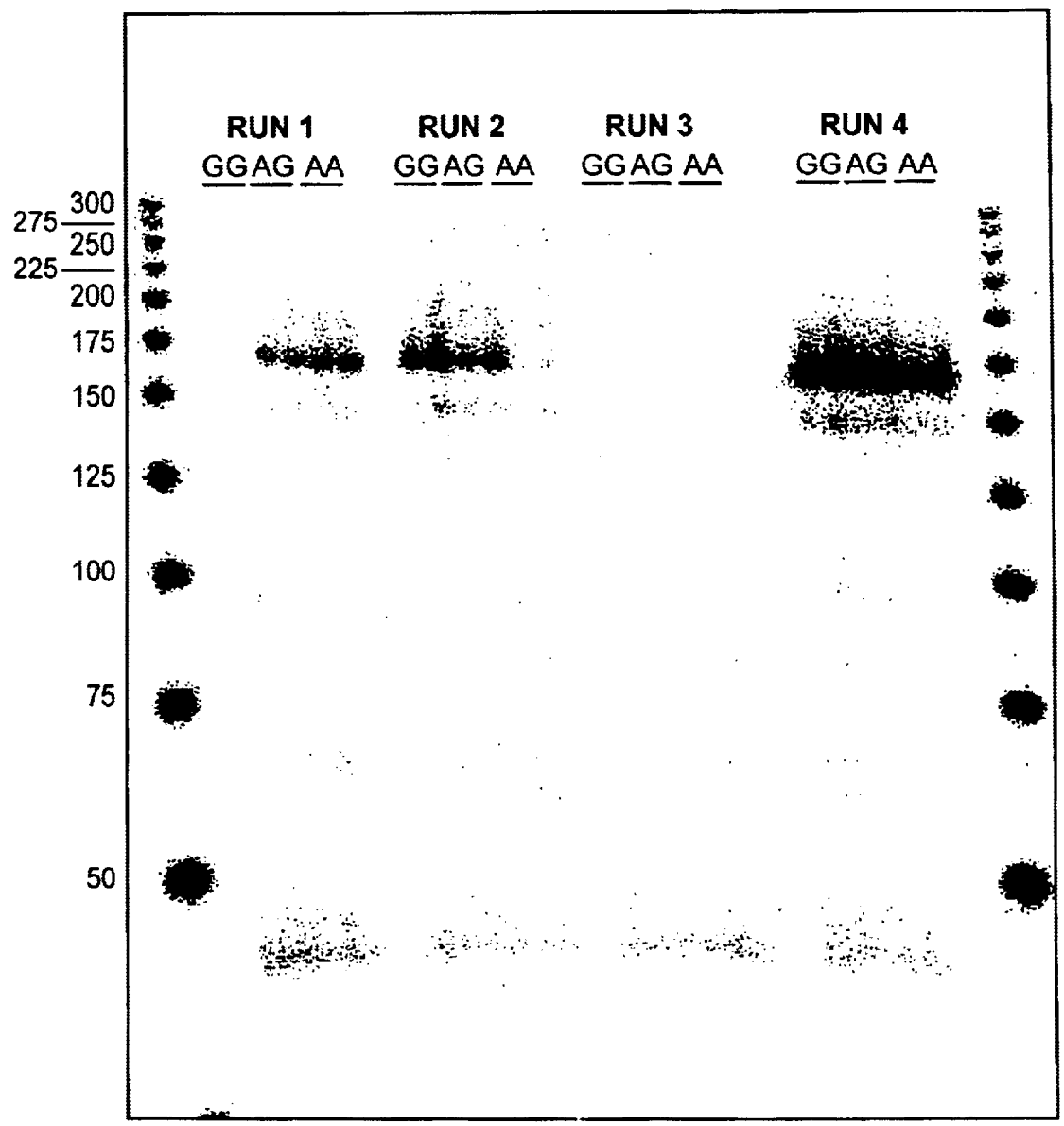
FIG. 3 shows results from a gel where polymorphic variant probes are selectively employed to block polymorphic variants of the target nucleic acid sample.

It is possible to avoid detecting a polymorphic variant as a false positive on a target nucleic acid. This provides an opportunity for de novo alteration detection on such targets. FIG. 3 illustrates methods of the invention employed to block the G→A polymorphism at codon 1493 of the APC mutation cluster region, to enable de novo detection.

Any biological sample that comprises an associated polymorphism may be used, for example, a tissue, stool or blood sample. For this analysis, blood samples from six individuals were separately tested. The sample set included a polymorphic variant base at codon 1493. For the purposes of a control in this experiment, genotype sequencing was performed on the six individual samples prior to performing the analysis illustrated in FIG. 3. The control sequence confirmed that the sample set being tested included two homozygous individuals having two G bases, two homozygous individuals having an A base and a G base, and two homozygous individuals having two A bases.

Each individual sample was analyzed as follows. Nucleic acid was extracted from each individual blood sample. The nucleic acid was then mixed with magnetic streptavidin coated Dynal beads, which provided a solid phase matrix. The nucleic acid and bead mixture was vortexed and incubated to bind the beads to the nucleic acid. The nucleic acid was thereafter amplified by PCR, which required the nucleic acid template to be mixed with binding and wash buffers. During the PCR process, the reverse PCR primer was biotinylated. The PCR product was denatured and made single stranded. The nucleic acid mixture was vortexed. The supernatant was removed, and buffer was added.

Nucleic acid probes were designed to compliment the target nucleic acid including the polymorphic variants in codon 1493 of the APC mutation cluster region. The probes are uniform in length are 17 base pairs long. The probes are designed so that after hybridization the probe positioned second in from the free end of the target nucleic acid (i.e., the end of the target nucleic acid that is not bound to the bead) has a P32 reporter on its 5' end. The probes and the target nucleic acid are hybridized at 59° C. for one hour. The hybridization solution was a mixture of 3 molar tetramethyl ammonium chloride (TMA); 1 mM EDTA; 10 mM phosphate buffer at a pH of 6.8; 5X of Denhardts solution; 0.04 mg/ml of yeast RNA; SDS at 0.1% of the mixture and between about 0.04 micromolar and about 0.64 micromolar of the probe mixture. The tube is exposed to a magnet that attracts the magnetic beads and retains the target nucleic acid that is bound to the beads and the supernatant is removed.

After hybridization, the unhybridized probes were removed by washing the nucleic acid mixture under conditions that preserve the nucleic acid:probe hybrids. The hybridization solution was washed a series of times under varying time and temperature conditions. The wash solution contained a mixture of 3 molar tetramethyl amonium chloride (TMA); 1 mM EDTA; 10 mM phosphate buffer at a pH of 6.8; and SDS at 0.1% of the mixture. After each wash, the tube is exposed to a magnet that attracts the magnetic beads and retains the target nucleic acid that is bound to the beads and the supernatant is removed. In the first wash, the hybridization solution was mixed with the wash solution at 59° C. for 15 minutes. Thereafter, in the second wash, the hybridization solution was mixed with the wash solution at room temperature, about 22° C., for 1 minute. In the third wash, the hybridization solution was mixed with a the wash solution at room temperature, about 22° C., for about 1 minute.

In a test tube, the target nucleic acid was exposed to 0.015 unit per microliter of the enzyme S1, in the buffer containing sodium acetate at 50 mM, NaCl at 280 mM, and $ZnSO_4$ at 4.5 mM, per microliter of the cutting reaction for thirty minutes at room temperature, about 22° C. The reaction is a 100 microliter reaction. Exposure to the enzyme S1 cleaves any single stranded regions of the target nucleic acid. The tube is exposed to a magnet to attract the magnetic beads and retain the target nucleic acid that is bound to the beads. The supernatant is pipetted out of the tube and mixed with a load dye.

The supernatant is run on a 6% non-denaturing acrylamide gel at a rate of 1,200 Volt hours. The gel is exposed to an instant imager, which picks up radioactivity. The gel is analyzed for fragment size and any cuts in the target nucleic acid can be determined by the size of the product on the gel.

Referring to FIG. 3, Run 1 shows experimental results where the six samples being tested were exposed to probes designed to complement the polymorphic variant where codon 1493 is a G. The six samples include two individuals having two G bases, two individuals having an A base and a G base, and two individuals having two A bases. Referring to the sample from the two individuals having two G bases, the product on the gel shows that exposure to the agent, S1, did not cut the target. The target nucleic acid was not cut because the probes designed to complement the polymorphic variant where codon 1493 is a G hybridized to the target nucleic acid of the two individuals having two G bases. Referring again to Run 1, samples from two individuals having an A base and a G base were exposed to the probes designed to complement the polymorphic variant where codon 1493 is a G. The probes hybridized to the G variant of the two individuals having an A base and a G base. However, no probe hybridized to the polymorphic variant of the target sample where codon 1493 is an A and upon exposure to the agent S1, the single stranded region at codon 1493 was cut generating product on the gel. Finally, in Run 1, samples from two individuals having two A bases were exposed to the probes designed to complement the polymorphic variant where codon 1493 is a G. No probe hybridized to the polymorphic variant of the two individuals having two A bases, and exposure to the agent, S1, cut the target at the region of the polymorphic variant generating product on the gel.

Referring to FIG. 3, Run 2 shows experimental results where the six samples being tested were exposed to probes designed to complement the polymorphic variant where codon 1493 is an A. Again, the six samples include two individuals having two G bases, two individuals having an A base and a G base, and two individuals having two A bases. Referring to the sample from the two individuals having two G bases, the product on the gel shows exposure to the agent, S1, cut the target at the region of the polymorphic variant leaving product on the gel. The target nucleic acid was cut because the probes including the polymorphic variant where codon 1493 is A failed to hybridize to the target nucleic acid of the two individuals having two G bases. Referring again to Run 2, samples from two individuals having an A base and a G base were exposed to the probes designed to complement the polymorphic variant where codon 1493 is an A. The probes hybridized to the A variant of the two individuals having an A base and a G base. However, no probe hybridized to the polymorphic variant of the target sample where codon 1493 is G and upon exposure to the agent S1, the single stranded region at codon 1493 was cut generating product on the gel. Finally, in Run 2 samples from two individuals having two A bases were exposed to the probes designed to complement the polymorphic variant where codon 1493 is a A. The product on the gel shows exposure to the agent, S1, did not cut the target. The target nucleic acid was not cut because the probes designed to complement the polymorphic variant where codon 1493 is an A hybridized to the target nucleic acid of the two individuals having two A bases.

Referring to FIG. 3, Run 3 shows experimental results where the six samples being tested were exposed to two different sets of probes: one designed to complement the polymorphic variant where codon 1493 is an A and one designed to complement the polymorphic variant where codon 1493 is a G. Again, the six samples include two individuals having two G bases, two individuals having an A base and a G base, and two individuals having two A bases. Referring again to Run 3, exposure to sets of probes designed to complement both the polymorphic variant A and the polymorphic variant G succeeds in blocking the codon 1493 region in all six samples. Thus, both polymorphic variant probes successfully block the polymorphic variants on the target nucleic acids tested and, according to methods of the invention, any other alterations on the target may be detected.

Finally, referring to FIG. 3, Run 4 shows experimental results where, again, six samples were tested, the samples from two individuals having two G bases, two individuals having an A base and a G base, and two individuals having two A bases. The six samples being tested were exposed to probes where no probe was designed to complement the polymorphic variants present in the six samples. Referring again to Run 4, upon exposure to the agent S1, the single stranded region at codon 1493 for both the polymorphic variant where codon 1493 is an A and the polymorphic variant where codon 1493 is a G was cut generating product on the gel. Thus, according to methods of the invention, probes may be designed to block the G→A polymorphism at codon 1493 of the APC to enable detection of other alterations in the target nucleic acid.

What is claimed is:

1. A method for detecting an alteration in a target nucleic acid suspected to be in a biological sample, the method comprising the steps of:

a) adding, to a biological sample suspected to contain a target nucleic acid, a plurality of single-stranded peptide nucleic acids that hybridize contiguously to a region of said target nucleic acid if said region is unaltered;
   b) adding to said biological sample an agent that degrades single-stranded nucleic acids; and,
   c) detecting an alteration in said target nucleic acid as the presence of a degradation product from steps a) and b) resulting from degradation within said region of said target nucleic acid.

2. The method of claim 1, wherein said alteration is a disease-associated mutation.

3. The method of claim 2, wherein said disease is cancer.

4. The method of claim 2, further comprising the step of determining the identity of said alteration in said target nucleic acid.

5. The method of claim 1, wherein at least one member of said plurality of single-stranded peptide nucleic acids comprises a detectable label.

6. The method of claim 1, wherein said target nucleic acid suspected of being in said biological sample comprises a detectable label.

7. The method of claim 5 or 6, wherein said detectable label is selected from the group consisting of a fluorescent tag, a radioactive isotope, and a molecular weight marker.

8. The method of claim 1, wherein each member of said plurality of single-stranded peptide nucleic acids is between about 8 and about 30 nucleotides long.

9. The method of claim 1, wherein each member of said plurality of single-stranded peptide nucleic acids has an approximately equivalent hybridization melting temperature.

10. The method of claim 1, wherein said target nucleic acid is bound to a solid support.

11. The method of claim 10, wherein the 5' of said target nucleic acid is bound to said solid support.

12. The method of claim 10, wherein the 3' end of said target nucleic acid is bound to said solid support.

13. The method of claim 1, wherein said biological sample comprises a tissue or body fluid.

14. The method of claim 1, wherein said agent is an enzyme.

15. The method of claim 14, wherein said enzyme is selected from the group consisting of S1, MutY, MutS, and Mungbean nuclease.

16. The method of claim 1, wherein said agent is a chemical agent.

17. The method of claim 2, wherein said alteration is selected from the group consisting of nucleotide insertions, deletions, rearrangements, transitions, translations, transversions, and substitutions.

18. The method of claim 13, wherein said tissue or body fluid is selected from the group consisting of sputum, pancreatic fluid, bile, lymph, plasma, urine, cerebrospinal fluid, seminal fluid, saliva, breast nipple aspirate, pus, biopsy tissue, fetal cells, and amniotic fluid.

19. The method of claim 13, wherein said tissue or body fluid is a stool sample.

20. The method of claim 1, wherein said alteration is a single nucleotide polymorphism.

21. The method of claim 1, wherein said alteration is inherited.

22. The method of claim 1, wherein said alteration exists as a subpopulation in a heterogeneous sample.

23. A method for detecting an alteration in a target nucleic acid suspected to be in a biological sample, the method comprising the steps of:

a) adding, to a biological sample suspected to contain a target nucleic acid, a plurality of probes that hybridize to a region of said target nucleic acid such that a gap separates adjacent hybridized probes, if said region is unaltered;

b) adding to said biological sample an agent under conditions that degrade single-stranded nucleic acids larger than said gap size; and, c) detecting an alteration in said target nucleic acid as the presence of a degradation product from steps a) and b) resulting from degradation within said single-stranded region of said target nucleic acid.

24. A nethod for detecting an alteration in a polymorphic target nucleic acid suspected to be in a biological sample, the method comprising the steps of:

a) adding, to a biological sample suspected to contain a polymorphic target nucleic acid, a plurality of probes, said plurality comprising a probe complementary to each polymorphic varient of said target nucleic acid, such that said probes hybridize contiguously to a region of said target nucleic acid if said region is unaltered;

b) adding to said biological sample an agent that degrades single-stranded nucleic acids; and, c) detecting an alteration in said target nucleic acid as the presence of a degradation product from steps a) and b) resulting from degradation within said region of said target nucleic acid.

* * * * *